US010434514B2

(12) United States Patent
Kolesnychenko et al.

(10) Patent No.: US 10,434,514 B2
(45) Date of Patent: Oct. 8, 2019

(54) THERMAL CYCLING SYSTEM COMPRISING TRANSPORT HEATER

(75) Inventors: Aleksey Kolesnychenko, Eindhoven (NL); Martinus L. J. Geijselaers, Eindhoven (NL)

(73) Assignee: Biocartis S.A., Mechelen (BE)

( * ) Notice: Subject to any disclaimer, the term of this patent is extended or adjusted under 35 U.S.C. 154(b) by 0 days.

(21) Appl. No.: 13/131,511

(22) PCT Filed: Nov. 18, 2009

(86) PCT No.: PCT/IB2009/055134
§ 371 (c)(1),
(2), (4) Date: May 26, 2011

(87) PCT Pub. No.: WO2010/064160
PCT Pub. Date: Jun. 10, 2010

(65) Prior Publication Data

US 2011/0236901 A1 Sep. 29, 2011

(30) Foreign Application Priority Data

Dec. 5, 2008 (EP) .................................... 08170837

(51) Int. Cl.
*C12M 1/00* (2006.01)
*H05B 3/10* (2006.01)
(Continued)

(52) U.S. Cl.
CPC . *B01L 7/52* (2013.01); *B01L 9/52* (2013.01); *B01L 2200/147* (2013.01);
(Continued)

(58) Field of Classification Search
CPC ...... B01L 7/52; B01L 9/52; B01L 2300/0654; B01L 2200/147; B01L 2300/12; B01L 2300/1827
(Continued)

(56) References Cited

U.S. PATENT DOCUMENTS 4,234,540 A 11/1980 Ginsberg et al.
5,486,335 A * 1/1996 Wilding .............. B01F 15/0264
366/DIG. 3
(Continued)

FOREIGN PATENT DOCUMENTS

EP 1 926 010 A 5/2008
JP 10-96725 A 4/1998
(Continued)

OTHER PUBLICATIONS

Action from the Japanese Patent Office dated Sep. 17, 2013 for Japanese Application No. 2011-539125.
(Continued)

*Primary Examiner* — Liban M Hassan
(74) *Attorney, Agent, or Firm* — Ladas & Parry LLP

(57) ABSTRACT

To provide a thermal cycling system allowing an efficient thermal cycling and an optical detection during the diagnostic process a thermal cycling system is proposed, comprising: at least one heating device (10*a*, 10*b*) having a transparent substrate (11*a*, 11*b*) and a heating element (12*a*, 12*b*), and a chamber (30) adapted to receive a sample, the chamber (30) is placed adjacent to at least one heating device (10*a*, 10*b*), wherein at least a part of the chamber (30) comprises a transparent area (31) aligned with the transparent substrate (11*a*, 11*b*) of the at least one heating device (10*a*, 10*b*). Thereby, the speed and efficiency of the thermal system is increased. Moreover, an optical detection of the sample is possible.

19 Claims, 2 Drawing Sheets

(51) Int. Cl.
*B01L 7/00* (2006.01)
*B01L 9/00* (2006.01)

(52) U.S. Cl.
CPC ... *B01L 2300/0654* (2013.01); *B01L 2300/12* (2013.01); *B01L 2300/1827* (2013.01)

(58) Field of Classification Search
USPC ........................ 435/287.2, 6.12, 289.1, 292.1
See application file for complete search history.

(56) References Cited

U.S. PATENT DOCUMENTS

| | | | | |
|---|---|---|---|---|
| 5,567,617 | A * | 10/1996 | Caprio | B01L 7/52 435/287.2 |
| 5,846,487 | A | 12/1998 | Bennett, II | |
| 5,939,312 | A * | 8/1999 | Baier | B01L 3/502707 422/50 |
| 6,071,480 | A | 6/2000 | Halaka | |
| 6,318,158 | B1 | 11/2001 | Breen et al. | |
| 6,337,435 | B1 * | 1/2002 | Chu et al. | 136/242 |
| 6,396,581 | B1 | 5/2002 | Hayashi et al. | |
| 6,403,037 | B1 * | 6/2002 | Chang et al. | 422/68.1 |
| 6,596,483 | B1 * | 7/2003 | Choong | G01N 21/6452 377/60 |
| 6,699,711 | B1 | 3/2004 | Hahn et al. | |
| 6,960,437 | B2 * | 11/2005 | Enzelberger et al. | 435/6.19 |
| 7,189,367 | B2 * | 3/2007 | Yamamoto | B01J 19/0093 204/193 |
| 7,507,575 | B2 | 3/2009 | Bedingham et al. | |
| 7,757,561 | B2 | 7/2010 | Laugharn, Jr. et al. | |
| 2002/0168299 | A1 * | 11/2002 | Chang et al. | 422/102 |
| 2004/0053268 | A1 * | 3/2004 | Karlsen | 435/6 |
| 2004/0062468 | A1 | 4/2004 | Lee | |
| 2006/0030035 | A1 * | 2/2006 | Joseph et al. | 435/288.4 |
| 2006/0078929 | A1 | 4/2006 | Bickel et al. | |
| 2007/0196237 | A1 * | 8/2007 | Neuzil | B01L 3/50851 422/67 |
| 2007/0275415 | A1 * | 11/2007 | Srinivasan | B01F 13/0071 435/7.4 |
| 2008/0032347 | A1 | 2/2008 | Sarofim et al. | |

FOREIGN PATENT DOCUMENTS

| | | | | |
|---|---|---|---|---|
| JP | 2005-181143 | A | 7/2005 | |
| JP | 2006-201120 | A | 8/2006 | |
| JP | 2006-523095 | A | 10/2006 | |
| JP | 2008-145125 | A | 6/2008 | |
| JP | 2008-151772 | A | 7/2008 | |
| JP | 2008-232798 | A | 10/2008 | |
| JP | 2008-278791 | A | 11/2008 | |
| WO | 2001/57253 | A | 8/2001 | |
| WO | WO 2005065827 | A1 * | 7/2005 | B01L 7/52 |
| WO | WO 2007120829 | A2 * | 10/2007 | A01N 1/02 |
| WO | 2008/002563 | A2 | 1/2008 | |
| WO | 2009/019448 | A2 | 2/2009 | |
| WO | 2010/118540 | A1 | 10/2010 | |
| WO | 2010/118541 | A1 | 10/2010 | |
| WO | 2010/118542 | A1 | 10/2010 | |

OTHER PUBLICATIONS

Action from the Japanese Patent Office dated Oct. 7, 2013 for Japanese Application No. 2012-505018.
Espacenet English abstract of JP 2006-201120 A.
Espacenet English abstract of JP 2006-523095 A.
Espacenet English abstract of JP 2008-278791 A.
Espacenet English abstract of JP 2008-151772 A.
Espacenet English abstract of JP 2008-232798 A.
Espacenet English abstract of JP 2008-145125 A.
Espacenet English abstract of JP 2005-181143 A.
Espacenet English abstract of JP 10-96725 A.

* cited by examiner

THERMAL CYCLING SYSTEM COMPRISING TRANSPORT HEATER

FIELD OF THE INVENTION

The invention relates to a thermal cycling system and to a diagnostic device. Moreover, it relates to a use of the thermal cycling system in a DNA amplification process.

BACKGROUND OF THE INVENTION

In molecular diagnostic amplifications, the DNA from a sample, like blood, stool, etc. is multiplied or copied in order to raise the amount of DNA above a detection threshold. Various amplification processes exist. Moreover, in diagnostic applications, there is need for thermal cycling processes required for controlling a heating or cooling of a sample or mixture, which is monitored or analyzed during diagnostic application. In particular, for many amplification processes thermal cycling is necessary because different steps during the amplification process take place at different temperatures. The DNA resulting from the amplification process is often detected optically, for instance by using flourophores in the amplification process.

Moreover, also for general diagnostic applications, samples or mixtures to be monitored or analyzed needs to be checked optically by a user or a monitoring device. Consequently, a very efficient thermal cycling system and an optical detection are required in general diagnostic applications and in particular in a DNA amplification process.

US 2008/0032347 A describes a temperature sensing element for monitoring heating and cooling. The system includes a cartridge for accommodating a chamber including a mixture to be analyzed. The cartridge is brought into contact with a device including a sensor layer, a heat conducting layer and a heating layer.

WO2001057253 A1 describers a thermal cycling system in which a chamber is placed between heaters and in which light is coupled into and out of the chamber through transparent sides of the chamber.

SUMMARY OF THE INVENTION

It is therefore an object of the present invention to provide a thermal cycling system and a heating system allowing an efficient thermal cycling and an optical detection during the diagnostic process.

The object is solved by the features of the independent claims. Preferred embodiments are given in the dependent claims.

The invention is based on the thought to provide a thermal cycling system comprising a heating device located adjacent to a chamber including the sample to be analyzed. The heating device includes a transparent substrate and a heating element for providing heat, which is conducted by the transparent substrate to the chamber and the sample to be analyzed.

The transparent substrate allows a user or a monitoring device to view through the transparent substrate of the support plate to thereby monitor the sample inside the chamber. Moreover, the chamber including the sample to be analyzed includes at least one part, which is transparent. The transparent area of the chamber is aligned with a transparent substrate of the heating device. By this, it is achieved to optically detect or monitor the sample during the diagnostic process. Consequently, the transparency of the substrate and the transparent area of the chamber should be such that optical detection or monitoring of the sample is possible. The heating element of the thermal cycling system allows a reliable thermal cycling of the chamber and the sample included in the chamber. Moreover, by combining the heating element and the transparent substrate a very efficient thermal contact is made between the heating element and the transparent substrate. The heating element may be placed on of the sides of the transparent substrate, in particular on top or below the transparent substrate. Further, it could be included inside the transparent substrate to improve the efficiency of the thermal conduction of the heat generated by the heating element.

Preferably, the transparent substrate and the transparent area of the chamber have a transmission better than 80% in the wavelength range of 300-1000 nm.

In a preferred embodiment of the invention, the thermal cycling system is arranged for coupling light from a light source into the chamber and/or coupling light emanating from the chamber to a detector through the transparent substrate. This embodiment has the advantage that coupling light through the transparent substrate offers an alternative optical interface to the chamber as compared to, for instance, coupling light into and out of the chamber through the minor surfaces (the smaller side surfaces of that chamber in a flat box geometry as opposed to the larger major surfaces) of the chamber. Coupling light through the minor surfaces of the chamber, as is done in the prior art, leaves the major surfaces of the chamber free to contact heaters in order to heat the sample inside the chamber. The chamber according to the prior art may have a flat geometry to allow quick thermal cycling through the major surfaces using the heaters and optical interfaces through the minor surfaces. However, according to the invention, the major surfaces of the transparent substrate, or in fact any surface of the transparent substrate, can be used as an optical interface to couple light into and/or out of the chamber. This offers possibilities for greater design freedom in arranging a light source and/or a detector, that may be comprised in the thermal cycling system, relative to a chamber. Another possibility offered by the invention is to gather more light from a chamber than possible through the minor surfaces of a chamber. The substrate may even comprise scattering centres to scatter light coming from the chamber towards a detector.

In a preferred embodiment of the invention, the light from the light source and/or the light emanating from the chamber is coupled through a major surface of the transparent substrate and the transparent area. This embodiment has the advantage that it enables more light from the light source to be coupled into the chamber and/or more light emanating from the chamber to be coupled to the detector than would be possible if the chamber were optically coupled to its surroundings through the minor surfaces, that is the side walls, of the transparent substrate. Moreover, this geometry allows for a compact arrangement of heaters, sample chamber, light source, and detector, for instance by having a light source and a detector at one side of the chamber and using a beam splitting element like a dichroic mirror to guide light from the light source to the chamber and from the chamber to the detector. Moreover still, this geometry has the advantage that it enables a single light source unit and/or a single detector unit to be used with respect to a plurality of chambers. The light source unit and/or detector unit can be moved from one chamber to the next one without the need for strict alignment between the light source, chamber, and detector that applies when using the minor surfaces of the chamber to couple light into and/or out of the chamber.

In a preferred embodiment of the invention, the chamber is placed between a first and second heating device, wherein the first heating device is placed on an upper side and the second heating device is placed on a lower side of the chamber. At least one of the upper or lower heating devices comprises a transparent substrate, wherein the corresponding side of the chamber also includes the transparent area, which is aligned to the transparent substrate of the heating device having the transparent substrate. By this, it is possible to optically detect for example a fluorescence light through the transparent substrate of the heating device and the transparent area of the chamber from one side of the thermal cycling system. Moreover, this embodiment provides the possibility to manufacture the other of the heating devices by a low price material without a transparent substrate. Preferably, the heating device realized without a transparent substrate includes a heating element for heating the chamber and the sample inside the chamber.

However, certain applications may require an upper and a lower heating device, which both comprise a transparent substrate. Thus, it is possible to optically detect the content of the chamber from both sides. By this, it is possible to place the chamber between the upper and lower heating devices without taking care where the respective transparent area of the chamber is located.

Preferably, the transparent substrate has a heat conductivity lower than 120 W/cm*K. Moreover, it is advantageously to provide a transparent substrate material having a low specific heat value. Normally for thermal heating systems aluminum is used as basic material providing a good heat conductivity of 117 W/cm*K at 20° C. To provide a very efficient heating of the sample in the chamber, the heat conductivity of the support plate should be at least similar to that of aluminum.

Moreover, it is preferred to have a low specific heat value, since the specific heat value determines the thermal mass of the heating element. Low thermal mass allows fast thermal cycling. A specific heat value for aluminum is about 0.9 J/g*K. A material having such requirements and which is transparent is sapphire. Sapphire has at 20° C. a heat conductivity of 100 W/cm*K which is lower than the heat conductivity of aluminum. The specific heat value for sapphire is 0.7 J/g*K. Thus, sapphire combines advantages of good heat conductivity and low specific heat value together with the transparent characteristic.

Combining the transparent material and the above mentioned characteristics a fast thermal cycling of the sample together with optically monitoring is possible. By simultaneously thermal cycling and optical detecting it possible to reduce the assay time drastically. Even, when performing the thermal cycling first and then detecting any optical signals, this could be performed very easily without any further handling steps, like removing the chamber out of the thermal cycling system for optical detecting etc.

The heating device may include only a transparent substrate and the heating element. But it is also possible to provide a support plate supporting the transparent substrate, wherein the heating element could be placed on both, the support plate and/or the transparent area. Then support plate could be realized non-transparent. However, when having two materials for the heating device the heat conductivities of both materials should be similar.

By providing the thermal cycling system having a transparent substrate made of sapphire it is possible to form a real time PCR (rtPCR) requiring simultaneously thermal cycling of sample liquid and optical detection of fluorescence signals originating from the DNA amplification. By this, the DNA amplification speed is increased due to the efficiency and speed of the thermal cycling system. Therefore the thermal cycling system of the present invention provides a very fast thermal system in order to decrease the assay time. In addition, such thermal cycling system provides a very good optical access to the chamber and in particular to the sample liquid included in the chamber in order to be able to perform an optical detection simultaneously or sequentially to the thermal cycling process.

In a further preferred embodiment, the heating element is also made of a transparent material, for instance Indium oxide. By this the heating element does not interfere with the detection of fluorescence signals originating from the sample to be analyzed. The heating element could be placed between the transparent substrate and the chamber or could be integrated into the transparent substrate, for instance in a groove of the transparent substrate. Alternatively, the heating element may be arranged on the chamber opposing side of the transparent substrate. However, in case of having a support plate supporting the transparent substrate the heating element could also be placed respective sides of the support plate or could be integrated into the support plate.

Preferably, the heating elements of the upper and lower heating device are shaped similarly.

Moreover, to control the thermal cycling process of the sample inside the chamber, the thermal cycling system includes at least one temperature sensor, which is coupled to the heating device for detecting the temperature of the transparent substrate to detect the process temperature of the chamber.

The sensor could be placed in a groove of the transparent substrate, between the chamber and the transparent substrate or on the chamber opposing side. Further it could be integrated into a cartridge accommodating the chamber. By providing the temperature sensor into a groove of the transparent substrate, a better temperature sensoring is achieved.

The heating element used for heating the sample inside the chamber is preferably realized as a resistive heating element. The heating element (in, for instance, at least one of the heaters in a thermal cycling system) could be realized as wire embedded into a groove of the transparent substrate or it could have a flat shape, which is placed between the transparent substrate and the chamber or on the chamber opposing side. It is preferably realized as a thin film heater. However, it could also be realized as a heating wire, which is then placed into a groove of the support plate to provide good thermal contact of the heating element. The heating element is formed as a ring to thereby form a substrate window inside the ring, which is used for optical detecting the sample inside the chamber and for optical detecting an optical signal of the sample inside the chamber. The substrate window should be aligned to a transparent area of the chamber.

Preferably, the chamber includes a top and a bottom face, wherein at least one of the top or bottom face comprises a transparent area realized as transparent foil. The transparent foil allows directing an excitation signal onto the sample and to detect an optical signal originated from the sample. Moreover, the transparent foil is made of an elastic transparent foil. Thus, by thermal heating the chamber the foil will blow up in the direction of the heating device. However, the blowing up is limited by the transparent substrate to thereby increase the pressure inside the chamber to further speed up the thermal cycling process and to increase the thermal contact between the transparent substrate and the chamber. Further, the formation of air bubbles inside the chamber is thereby prevented.

The thermal cycling system further includes at least one holder for holding the heating device and particular for holding the heating element and/or the transparent substrate. The holder includes an opening for providing free optical access to the substrate window. T The holder preferably holds the support plate and/or the support plate at its edge respectively. Preferably, the holder contacts the ring-shaped heating element, which is placed on the chamber opposing side. Thus, the heating element is placed below the holder and is pressed by the holder in direction of the transparent substrate and the chamber. For providing the required force, the holder is coupled to a mechanical spring, which is pressing the transparent substrate and/or the heating element against the chamber to thereby increase the mechanical and the thermal contact between the heating device and the chamber.

Advantageously the thermal cycling system comprises a cartridge for accommodating the chamber.

The object is further solved by a heating device having at least one a transparent substrate and a heating element, wherein the transparent substrate is transparent to at least one of an excitation signal and a response to an excitation signal.

Thus, for instance, the sample, which is placed below or above the heating device. When exciting the sample could be excited by an optical excitation signal or monitored by a user and the response of the excitation signal could also be received via the transparent substrate of the heating device. Thereby, an efficient heating of the sample in parallel to the detecting or monitoring could be performed. This could be done simultaneously or sequentially. The preferred embodiments as described above for the thermal heating system could be applied also to the heating system.

The object is further solved by a diagnostic device including a cartridge having a plurality of thermal cycling systems as described above. Preferably, the cartridge includes a plurality of spaces for accommodating a plurality of chambers, which are then placed between an upper and lower heating devices, respectively.

Moreover, the object is solved by use of the thermal cycling system as described above in a DNA amplification process and in particular in a PCR process. Preferably, the thermal cycling system as described above is suited for being used in a real-time PCR process requiring a simultaneously thermal cycling and optical detecting.

A further advantage of using sapphire as material for the transparent substrate is that it is extremely hard and thereby ensures a long lifetime. Moreover, it has a very high chemical inertness allowing a simple cleaning process. Further, it provides a large wavelength range allowing optical detection of fluorescence signals for multiple dye labels. The thermal cycling system of the present invention is in particular applicable for DNA amplification processors. However, the thermal cycling system could also be used in the field of general molecular diagnostic, in the field of chemical diagnostics, in point of care diagnostics and in biomolecular diagnostic research. It could be used for biosensors, gene and protein expression arrays and environmental sensors and for heat quality sensors.

According to another aspect of the invention there is provided a method for diagnostically analyzing a sample, comprising the steps of: bringing a chamber including the sample to be analyzed in contact with at least one heating device having a transparent substrate and a heating element; thermal cycling the chamber by generating heat with the heating element conducted to the chamber via the transparent substrate; and optically detecting the sample inside the chamber sequentially or simultaneously to the thermal cycling step.

In the following various exemplary embodiments of the invention are described.

DETAILED DESCRIPTION OF THE EMBODIMENTS

Figure 1:
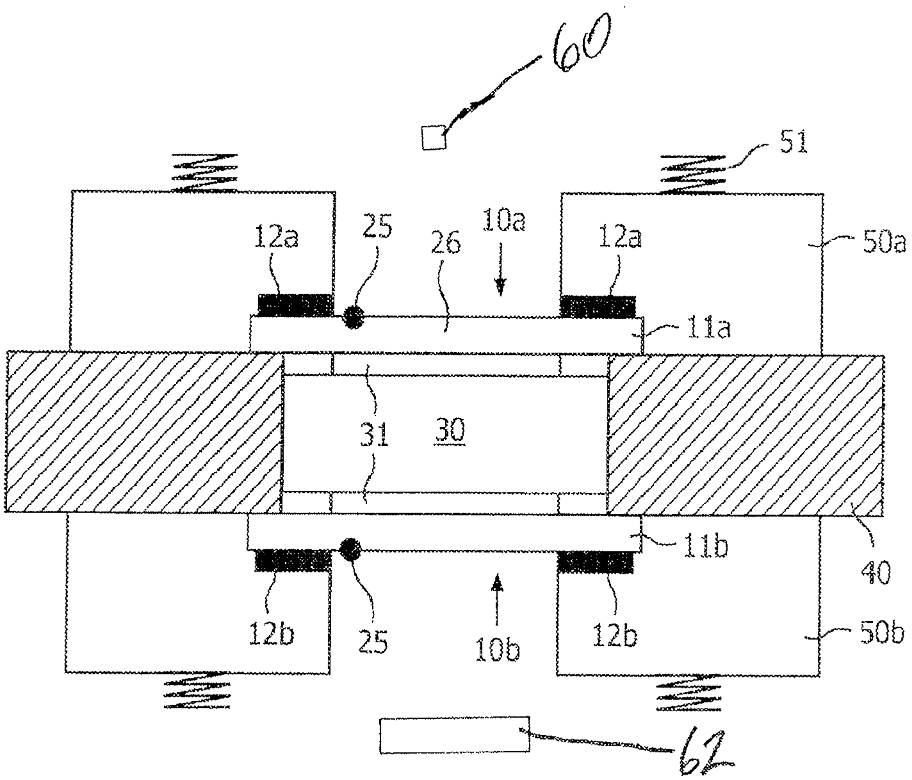
FIG. 1 shows a sectional view of the thermal cycling system according to the present invention

In FIG. 1 a sectional view of the thermal cycling system according to the present invention is shown. There are a first heating device 10*a* and a second heating device 10*b*. A chamber 30 is placed between the first and second heating device 10*a*, 10*b*. The chamber 30 is accommodated by a cartridge 40, which is only partly shown. A light source 60 may be provided to emit light that emanates through the chamber. A monitor or detector 62 may be provided to optically detect or monitor the sample.

The first and second heating device 10*a*, 10*b* of the embodiment shown in FIG. 1 includes a transparent substrate 11*a*, 11*b* made of sapphire. Thus, the transparent substrates 11*a*, 11*b* are completely transparent. It is not illustrated but possible to have a support plate supporting the transparent substrate in the middle thereof. Then the support plate is surrounding the transparent substrate. The support plate could have different material and could be transparent or non transparent.

The temperature sensor 25 may be arranged at each side of the chamber for sensing the temperature of the respective transparent substrates 11*a*, 11*b*. But, it may be sufficient to only have one temperature sensor. The temperature sensor 25 could be placed also inside the cartridge 40.

Figure 3:
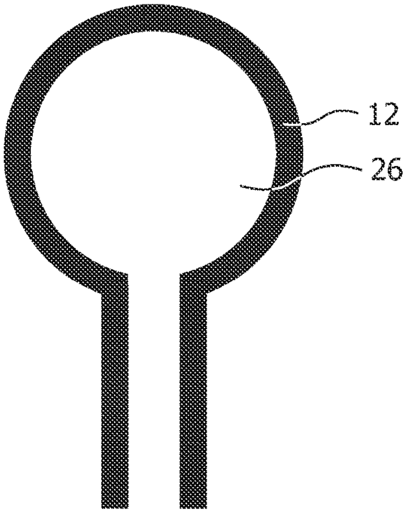
FIG. 3 shows a heating element in flat form according to the present invention.

The heating elements 12*a* and 12*b* are realized in flat form and have a ring-form as shown in FIG. 3. The flat form heating elements 12*a*, 12*b* are arranged on the respective chamber opposing sides of the heating devices 10*a* and 10*b*. However, also other forms of the heating elements are possible. Additionally the location of the heating elements 12*a*, 12*b* may be different to the embodiment as shown in FIG. 1. The heating elements 12*a*, 12*b* could be completely embedded inside the transparent material, preferably in a groove formed in the transparent substrate.

If the heating element is made of a transparent material it could also have a larger area than shown in FIG. 1, to thereby provide a better contact and a heat exchange between the heating element 12*a*, 12*b* and the transparent substrate 11*a*, 11*b*. If at least one of the heating elements 12*a*, 12*b* is transparent it may interfere with the substrate window 26, because optical detection is still possible.

The heating elements 12*a* and 12*b* and the transparent substrates 11*a* and 11*b* are respectively supported by holding elements 50*a* and 50*b*, which provide a reliable mechanical contact between the transparent substrate 11*a*, 11*b* and the heating elements 12*a*, 12*b* on the one hand and the chamber 30 on the other hand. By this, the heat generated by the heating elements 12*a* and 12*b* is transferred reliable by the transparent sapphire substrate 11*a*, 11*b* of the heating devices 10*a*, 10*b* to the chamber 30 for heating the sample included in the chamber 30.

The chamber includes a transparent area 31, which is realized as a transparent foil having elastic characteristic. When heating the chamber 30 containing the sample to be analyzed, the foil extends in direction of the transparent substrate 11*a*, 11*b*, thereby increasing the contact between the heating device 10*a*, 10*b* and the chamber 30.

The pressure for better heat conduction and contacting the heating element/transparent substrate with the chamber 30 could be increased by using springs 51 pressing the holding elements 50*a* and 50*b*, respectively in direction of the chamber 30 to thereby provide a close fitting between the transparent substrates 11*a*, 11*b* and the chamber 30.

Figure 2:
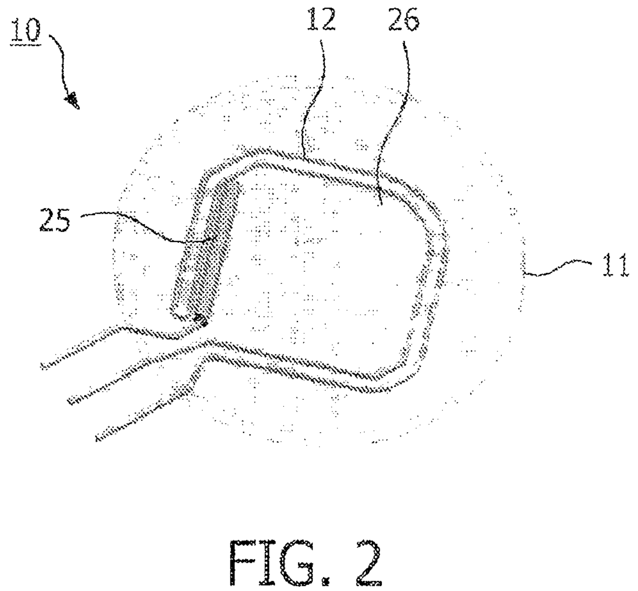
FIG. 2 shows a support plate including a heating wire according to the present invention.

In FIG. 2 a further embodiment of the heating device according to the present invention is illustrated. The heating device 10 shown in FIG. 2 includes a heating element 12 realized as a wire, which is formed in ring form having respective terminals for providing electrical connection to the resistive heating. Moreover, the transparent substrate 11 according to FIG. 2 includes a sensor 25, which is located inside the substrate window 26.

FIG. 3 illustrates an alternative realization of the heating element 12 according to the present invention. The heating element 12 is realized in flat form and directly placed on the chamber opposing side of the transparent substrate as shown in FIG. 1. Based on the large contact area between the flat form heating element 20 and the support plate 10 a good heat transmission from the heating element 12 to the transparent substrate 11 is provided. In case of using a wire as a heating element as shown in FIG. 2, it is preferred to provide a groove into the transparent substrate 11 to have a reliable heat transmission. It is not illustrated, but a further preferred solution to integrate or embed the heating element into the transparent substrate 11, to thereby increase the thermal contact between the heating element and the transparent substrate 11.

The temperature sensor 25 shown in FIG. 1 is preferably located inside the substrate window 26, wherein for reliable measuring the temperature, it is advantageously located in a groove of the transparent substrate 11. However, for measuring the temperature another location near the chamber may be used to thereby not to interfere the view or optical access into the chamber.

Figure 4:
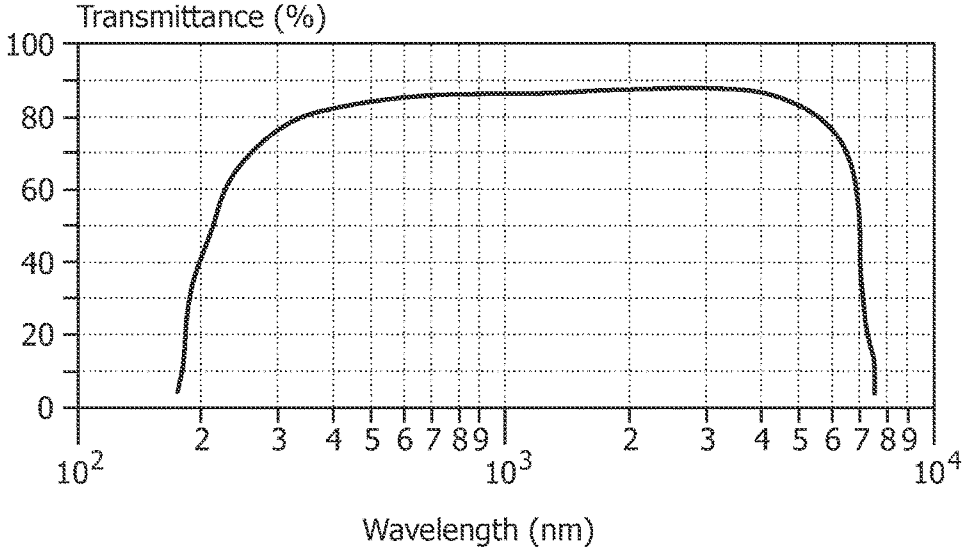
FIG. 4 shows a diagram showing the optical transmission of sapphire.

In FIG. 4 the optical transmission of sapphire material over a large wavelength range is shown, which allows an optical detection of fluorescence signals of multiple dye labels. Sapphire material as used preferably for the heating device provides a very good transmission rate from very low until very high wavelengths. Moreover, sapphire provides an extremely high hardness ensuring a long lifetime, wherein its chemical inertness allows a simple cleaning procedure.

Generally, the transparent substrate and the transparent area of the chamber are transparent to allow passing at least one of excitation light and a resulting fluorescence light. Thus, such optical signals must be able to pass through the heating device either to excite the sample or to reach a detector respectively.

A controller is provided to control the at least one heating element and the to receive the temperature value measured by the sensor. The controller may further control the optical excitation of the sample and the optical detection of the sample.

In a further aspect, it is also possible to use a heating device without a special chamber. Here, the sample to be analyzed is just placed below or above the heating device. By directing an excitation signal to the sample through the heating device and in particular through the transparent substrate the sample near the heating device could be excited and heated and monitored or detected as described above.

The thermal cycling system and the diagnostic device of the present invention are perfectly suited for a real-time PCR for an amplification process of DNA. By applying the invention in a DNA amplification process the speed of the thermal system is increased and thereby the efficiency. Moreover, an optical detection during the DNA amplification process is possible to detect a fluorescence signal originating from the DNA amplification. By using a transparent sapphire substrate together with a heating element in the inventive heating device, it is possible to easily optically detect the content of the PCR chamber.

The invention claimed is:

1. A thermal cycling system, comprising:

a plurality of heating devices for thermally cycling a sample, each of the plurality of heating devices comprising a transparent substrate with a major surface and a minor surface, each of the transparent substrates comprising sapphire and having a heating element integrated therein, the heating element of each of the transparent substrates being a resistive heating wire, a cartridge having at least one opening;

a chamber adapted to receive a sample, the chamber being accommodated in the at least one opening of the cartridge and formed as a component separate from the heating device, the chamber comprising a top face and a bottom face that define respective major surfaces of the chamber, each of the top and bottom faces comprising a transparent foil, the transparent foil of the top face being disposed adjacent the transparent substrate of a first of the plurality of heating devices such that, at least during operation, the transparent foil of the top face enters into contact with the major surface of the transparent substrate of the first of the plurality of heating devices, the transparent foil of the top face being sufficiently flexible such that it can expand toward the transparent substrate of the first heating device when the chamber is heated with the sample contained therein, the transparent foil of the bottom face being disposed adjacent the transparent substrate of a second of the plurality of heating devices such that, at least during operation, the transparent foil of the bottom face enters into contact with the major surface of the transparent substrate of the second of the plurality of heating devices, the transparent foil of the bottom face being sufficiently flexible such that it can expand toward the transparent substrate of the second heating device when the chamber is heated with the sample contained therein, the respective transparent foils of the top and bottom faces and the major surfaces of the respective transparent substrates of the first and second heating devices having a flat shape to facilitate thermal cycling through the respective major surfaces of the chamber; and a monitor, wherein the cartridge abuts the chamber without obstructing light from entering into or out of the chamber through the major surfaces of the chamber, wherein the heating wire of each of the transparent substrates is formed as a ring that forms a window through which light can pass; and wherein the transparent substrates of the first and second heating devices, the transparent foils of the top and bottom faces and the monitor are aligned such that light can pass through the transparent substrates and the transparent foils and to the monitor to permit the monitor to optically detect a sample in the chamber through the windows formed by the resistive heating wires of the respective transparent substrates.

2. The thermal cycling system according to claim 1, further comprising a light source disposed to emit light that passes through the transparent substrates and the transparent foils and to the monitor to permit the monitor to optically detect a sample in the chamber through the windows formed by the resistive heating wires of the respective transparent substrates.

3. The thermal cycling system according to claim 1, wherein the respective transparent foils of the top and bottom faces are disposed with respect to the major surfaces of the respective transparent substrates of the first and second heating devices so as to limit expansion of the respective transparent foils whereby to increase pressure inside the chamber when the chamber is heated and the respective transparent foils expand.

4. The thermal cycling system according to claim 1, wherein at least one of the plurality of heating devices comprises at least one sensor for detecting a temperature of the transparent substrate of the at least one of the plurality of heating devices.

5. The thermal cycling system according to claim 4, wherein the at least one sensor is disposed in a groove of the transparent substrate of the at least one of the plurality of heating devices.

6. The thermal cycling system according to claim 1, further comprising at least one holder that holds the plurality of heating devices.

7. The thermal cycling system according to claim 6, wherein the holder is coupled to a spring for pressing the transparent substrates of the first and second heating devices against the chamber.

8. The thermal cycling system according to claim 1, wherein each of the transparent substrates of the first and second heating devices has a specific heat value lower than 0.9 J/g*K.

9. The thermal cycling system according to claim 1, wherein the heating elements of each of the transparent substrates is transparent and is made of indium oxide.

10. The thermal cycling system according to claim 1, wherein the chamber occupies an entirety of the at least one opening of the cartridge.

11. A thermal cycling system, comprising:

at least one heating device for thermally cycling a sample, the at least one heating device comprising a transparent substrate with a major surface and a minor surface, the transparent substrate comprising sapphire and having a heating element integrated therein, the heating element being a resistive heating wire, a cartridge having at least one opening;

a chamber adapted to receive a sample, the chamber being accommodated in the at least one opening of the cartridge and being formed as a component separate from the at least one heating device, the chamber comprising a top face and a bottom face that define respective major surfaces of the chamber, each of the top and bottom faces comprising a transparent foil with the transparent foil of the top face being disposed adjacent the transparent substrate such that, at least during operation, the transparent foil enters into contact with the major surface of the transparent substrate and enables a thermal cycling of a sample in the chamber, the transparent foil of the top face being sufficiently flexible such that it can expand toward the transparent substrate when the chamber is heated with the sample contained therein; and a monitor, wherein the cartridge abuts the chamber without obstructing light from entering into or out of the chamber through the major surfaces of the chamber;

wherein the chamber occupies an entirety of the at least one opening of the cartridge;

wherein the heating wire of the transparent substrate is formed as a ring that forms a window through which light can pass; and wherein the transparent substrate, the transparent foil of the top face and the monitor are aligned such that light can pass through the transparent substrate and the transparent foil of the top face and to the monitor to permit the monitor to optically detect a sample in the chamber through the window formed by the resistive heating wire of the transparent substrate.

12. The thermal cycling system according to claim 11, further comprising a light source disposed to emit light that passes through the transparent substrate and the transparent foil and to the monitor to permit the monitor to optically detect a sample in the chamber through the window formed by the resistive heating wire of the transparent substrate.

13. The thermal cycling system according to claim 11, wherein the transparent foil and the major surface of the transparent substrate are flat in shape and the transparent foil is disposed with respect to the major surface of the transparent substrate so as to limit expansion of the transparent foil whereby to increase pressure inside the chamber when the chamber is heated and the transparent foil expands.

14. The thermal cycling system according to claim 11, wherein the at least one heating device comprises at least one sensor for detecting a temperature of the transparent substrate.

15. The thermal cycling system according to claim 14, wherein the at least one sensor is disposed in a groove of the transparent substrate.

16. The thermal cycling system according to claim 11, further comprising at least one holder that holds the at least one heating device.

17. The thermal cycling system according to claim 16, wherein the holder is coupled to a spring for pressing the transparent substrate against the chamber.

18. The thermal cycling system according to claim 11, wherein the transparent substrate has a specific heat value lower than 0.9 J/g*K.

19. The thermal cycling system according to claim 11, wherein the heating element is made of indium oxide.

* * * * *